United States Patent
Propp

(10) Patent No.: US 7,723,561 B2
(45) Date of Patent: *May 25, 2010

(54) PIV DRESSING ASSEMBLY

(75) Inventor: Donald J. Propp, Dewitt, MI (US)

(73) Assignee: Centurion Medical Products Corporation, Williamston, MI (US)

( * ) Notice: Subject to any disclaimer, the term of this patent is extended or adjusted under 35 U.S.C. 154(b) by 792 days.

This patent is subject to a terminal disclaimer.

(21) Appl. No.: 11/223,567

(22) Filed: Sep. 9, 2005

(65) Prior Publication Data

US 2007/0060892 A1   Mar. 15, 2007

(51) Int. Cl.
*A61F 13/00* (2006.01)

(52) U.S. Cl. .............. 602/58; 602/41; 602/42; 602/43; 602/52; 604/179; 604/180

(58) Field of Classification Search ........... 602/41–59; 604/179, 180; 128/888, 889, DIG. 26
See application file for complete search history.

(56) References Cited

U.S. PATENT DOCUMENTS

| | | | | |
|---|---|---|---|---|
| 2,897,961 | A * | 8/1959 | Bush | 206/441 |
| 6,124,520 | A * | 9/2000 | Roberts | 602/54 |
| 6,140,548 | A * | 10/2000 | Hansen et al. | 602/57 |
| 7,294,752 | B1 * | 11/2007 | Propp | 602/58 |
| 2004/0220505 | A1 * | 11/2004 | Worthley | 602/54 |
| 2005/0277888 | A1 * | 12/2005 | Propp | 604/174 |

* cited by examiner

*Primary Examiner*—Kim M Lewis
(74) *Attorney, Agent, or Firm*—Fildes & Outland, P.C.

(57) ABSTRACT

A PIV window dressing assembly with integral, built-in tubing anchors for the protection of a PIV catheter insertion site is disclosed that is interchangeably usable on both a right or left-hand side insertion site and that resists detachment from a patient's skin during use. The dressing assembly includes a fabric layer that is bounded by an edge. The fabric layer has an adhesive side, an opposite non-adhesive side, and at least one opening therein to allow for viewing therethrough. At least one reinforcement member is disposed between the fabric layer edge and the opening. The reinforcement member is adhered to the fabric layer adhesive side. A transparent film layer having an adhesive skin adhering side and an opposite non-adhesive side closes each of the openings in the fabric layer. The film layer non-adhesive side is adhered to the fabric layer adhesive side.

19 Claims, 5 Drawing Sheets

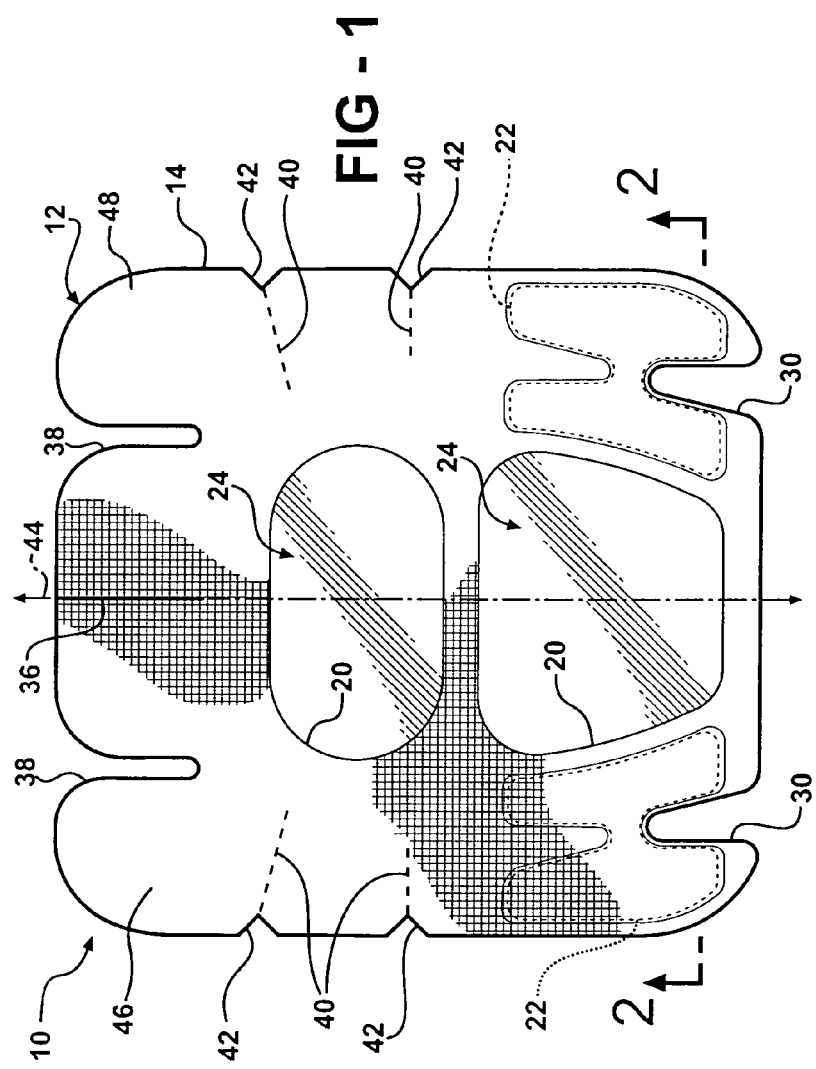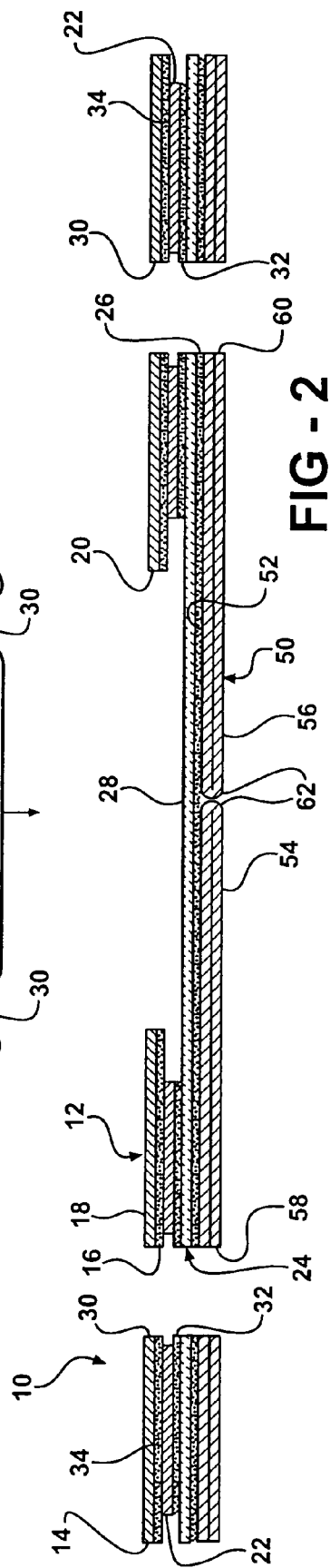

PIV DRESSING ASSEMBLY

TECHNICAL FIELD

This invention relates to medical dressings, and more particularly to dressing assemblies with integral built-in tubing anchors for the protection and securement of catheters and medical tubing about a PIV catheter insertion site on a patient's arm, hand, or fingers.

BACKGROUND OF THE INVENTION

It is known in the medical field that peripheral intravenous ("PIV") catheters have between a 20 and 70 percent failure rate, decreasing catheter dwell time from a potential between 72 and 96 hours to as low as merely 24 hours or less. Typically, these failures are caused by undesirable movement of the catheter. For example, the tubing, connectors, and fittings attached to the catheter are usually not well-secured and also hang over and off edges of a patient's body. Therefore, the tubing, connectors, and fittings may be bumped or pulled, which in turn causes the inserted catheter to move. Further, bumping or pulling of the tubing, connectors, and fittings loosens the catheter dressings, which then allows the catheter to more freely move.

Movement of an inserted catheter leads to catheter failure because the tip of the catheter pokes and scrapes the inner wall of the vein in which it is inserted. Poking and scraping of the vein wall leads to irritation of the vein and other complications, requiring premature removal of the catheter and insertion of the catheter in a different vein. This results in a waste of resources in both medical supplies and labor, as well as extended patient care and discomfort. Further, since each patient has a limited number of catheter insertion sites, it is undesirable to repeatedly replace a catheter at a new insertion site on a patient this process expends the available insertion sites.

In a specific example, PIV catheters are typically one to two inches in length and are inserted as low as the knuckles to as high as before the elbow. Usually, PIV catheters are first inserted on the hand. Since the tip of the catheter cannot be at the flex point of the wrist, there is only an area of approximately one to two inches on the hand to insert the PIV catheter. Therefore, the PIV catheter is usually inserted relatively low on the hand, which results in the tubing connected to the catheter, and sometimes the hub of the catheter itself, to overhang over the knuckles. This exposes the catheter and tubing to jarring, pulling, and pivoting. Further, the tubing connected to the catheter must be routed back towards the patient, necessitating the bending of the tubing 180 degrees from the connection of the tubing with the catheter. The bend in the tubing typically overhangs past the knuckle, and if not well-secured, can also cause movement or dislodgement of the catheter. These circumstances lead to a high failure rate for PIV catheters for the reasons described above, and therefore, there is a need to secure and prevent movement of PIV catheters and the tubing connected thereto.

SUMMARY OF THE INVENTION

The present invention provides a PIV dressing/anchor assembly with integral, built-in anchors that secures PIV catheters and resists movement of inserted catheters, significantly increasing catheter dwell time. The dressing assembly also secures and anchors tubing and fittings connected to the catheter. This prevents pulling forces on the tubing from transferring to and moving the catheter and/or from detaching the dressing from the patient, which would further expose the catheter to movement or even complete dislodgement from the vein.

More particularly, a PIV window dressing assembly in accordance with the present invention for the protection of a PIV catheter insertion site includes a fabric layer that is bounded by an edge. The fabric layer has an adhesive side, an opposite non-adhesive side, and at least one opening therein to allow for viewing therethrough. At least one reinforcement member is disposed between the fabric layer edge and the fabric layer opening. The reinforcement member is adhered to the fabric layer adhesive side. A transparent film layer having an adhesive skin adhering side and an opposite non-adhesive side closes each of the openings in the fabric layer. The film layer non-adhesive side is adhered to the fabric layer adhesive side.

Although the reinforcement member may take any shape and still accomplish its anchoring and force spreading/distributing function, in a specific embodiment, each reinforcement member may be generally of an H-like, or X-like, shape, and the dressing may include a recess in the fabric layer edge corresponding with each H-like, or X-like, shaped reinforcement member. Each reinforcement member may also have an adhesive side and an opposite non-adhesive side, the non-adhesive side being adhered to the fabric layer adhesive side.

Optionally, the PIV dressing assembly may include at least one slit in the fabric layer edge disposed along a length of the edge. Each slit may be disposed along a length of the fabric layer edge generally opposite the reinforcement member. Each slit may be one of a perforated line or a cut line. The PIV dressing assembly may also include a plurality of recesses disposed along the fabric layer edge along a length of the edge. The recesses may be disposed along a length of the edge generally opposite the reinforcement member. A portion of the fabric layer edge may have a curved shape disposed opposite the reinforcement member. At least one perforation line may extend inwardly from the fabric layer edge. The at least one perforation line may be disposed along a length of the fabric layer edge adjacent the reinforcement member. A landmark notch may be disposed along the fabric layer edge contiguous with each of the perforation lines for indicating the location of the perforation lines.

The dressing may have a central axis that spatially divides the dressing into first and second portions, the first and second portions being mirror images of each other. The dressing may also be generally rectangular in shape.

The PIV dressing assembly may further include a release liner having a tackless side contacting the adhesive side of the film layer. The release liner generally may extend to the edge of the fabric layer. The release liner may also include a first piece and a second piece. The first and second pieces may be folded such that each of the first and second pieces have a tab formed by the fold. One of the pieces can be released from the dressing without tampering with the other of the pieces.

The PIV dressing assembly may include a wallet, and the dressing may be folded and inserted into the wallet. The wallet may include a folded release liner.

The PIV dressing assembly may further include at least one closure member. Each closure member may have an adhesive side and an opposite non-adhesive side. Each closure member may be disposable on the fabric layer about the fabric layer edge at a location corresponding with a reinforcement member. One of the closure members may include a recess, and each of the closure members may generally have a circular shape. One or both of the closure members may serve as a patient, catheter, or dressing ID label.

These and other features and advantages of the invention will be more fully understood from the following detailed description of the invention taken together with the accompanying drawings.

BRIEF DESCRIPTION OF THE DRAWINGS

In the drawings:

FIG. 1 is a plan view of a PIV dressing assembly in accordance with the present invention;

FIG. 2 is a cross-sectional view of the PIV dressing assembly of FIG. 1;

DETAILED DESCRIPTION OF THE INVENTION

Figure 3:
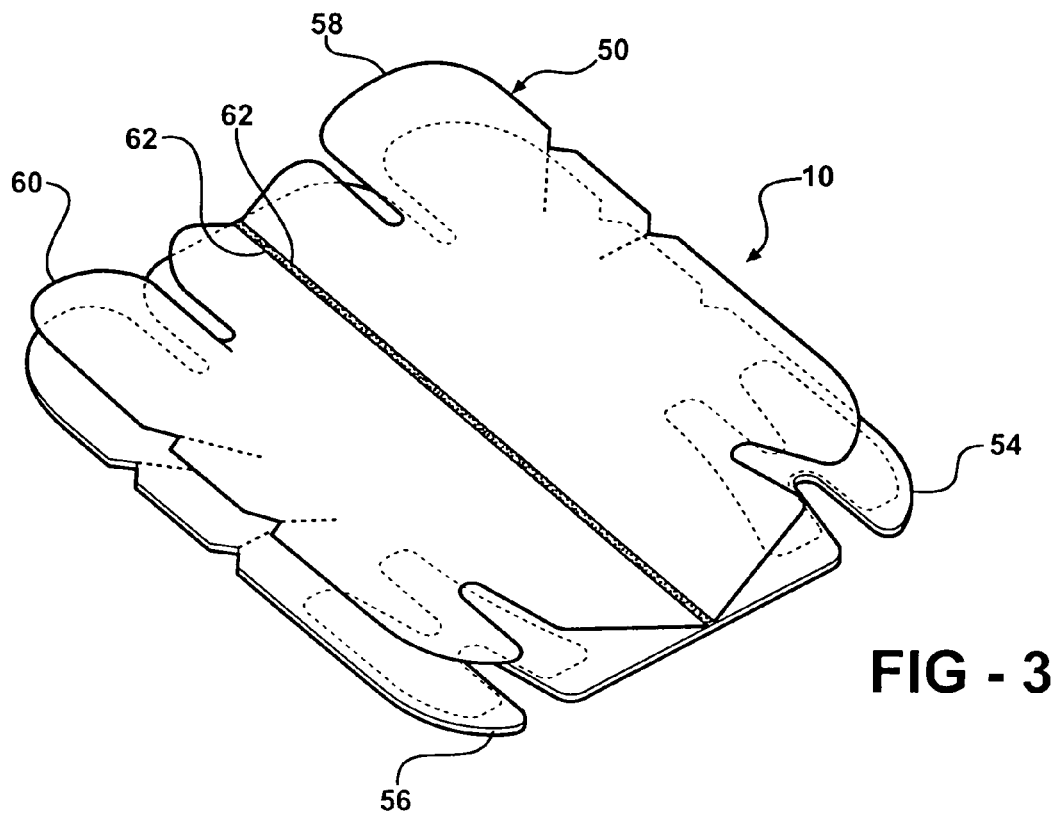
FIG. 3 is a perspective view of the PIV dressing assembly of FIG. 1 illustrating a release liner of the assembly.

Referring now to the drawings in detail, numeral 10 generally indicates a PIV dressing assembly in accordance with the present invention. The PIV dressing assembly secures PIV catheters and resists movement of catheters during use, allowing for an increase in catheter dwell time. The dressing assembly also secures and anchors tubing connected to the catheter, preventing forces exerted on the tubing from moving the catheter and/or from detaching the dressing from a patient. The dressing assembly may also be interchangeably usable on a catheter placed on a right-hand side or left-hand side of a patient, or on a more inward vein (closer to thumb) or on a more outboard (closer to pinkie) on either the left or right hand.

With reference to FIGS. 1 and 2, a PIV dressing assembly 10 in accordance with the present invention includes a fabric layer 12 that is bounded by an edge 14. The fabric layer 12 has an adhesive side 16, an opposite non-adhesive side 18, and at least one opening 20 therein to allow for viewing therethrough. The fabric layer 12 may be made of a woven or non-woven fabric, such as a non-woven polyester fabric or similar. The adhesive on the fabric layer adhesive side 16 may be any suitable medical grade adhesive such as an acrylic adhesive or similar. At least one reinforcement member 22 is disposed between the fabric layer edge 14 and the opening 20. The reinforcement member 22 is adhered to the fabric layer adhesive side 16. The reinforcement member 22 may be made of a netting, a mesh, or other similar material. A transparent film layer 24 having an adhesive skin adhering side 26 and an opposite non-adhesive side 28 closes each of the openings 20 in the fabric layer 12. The film layer non-adhesive side 28 is adhered to the fabric layer adhesive side 16. The film layer 24 may be made of a polyurethane material or similarly suitable transparent material. The adhesive on the film layer skin adhering side 26 may be any suitable medical grade adhesive.

As shown in FIG. 1, in a specific embodiment, the dressing 10 includes two openings 20. One of the openings 20 allows for the viewing of an insertion site, an inserted catheter, and a patient's skin surrounding the insertion site when the dressing is applied to a patient. The second opening 20 allows for the viewing of medical tubing, fittings, hubs, and/or connectors upstream of an inserted catheter. For example, medical personnel may use the second opening 20 to view for leaks in the tubing or air bubbles or blood backup in the tubing. Alternatively, the two openings 20 shown in FIG. 1 could be merged into one large opening. The narrow web between openings 20 gives strength to the generally very weak and very elastic film layer, which adds securement to catheters.

In this embodiment, the dressing 10 may have two reinforcement members 22. This allows the dressing to be equally useful on both the left-hand and right-hand side of a patient and on more inboard, or more outboard, catheter placements on either hand. Alternatively, the dressing could have one reinforcement member 22. Each reinforcement member 22 is arranged such that medical tubing exiting from underneath the dressing 10 may be anchored and supported by the reinforcement member 22. The reinforcement members 22 are thereby designed to reinforce the dressing 10 against being peeled away from a patient's skin by pulling forces exerted on the medical tubing. The reinforcement members 22 accomplish this by effectively spreading the pulling/peeling force over a larger surface area of the dressing 10, resulting in more skin to adhesive contact area. Due to the low elasticity of each reinforcement member 22 to which the highly elastic fabric layer 12 and film layer 24 are adhered, the reinforcement member 22 eliminates the typical prior art localized high pull force that is exerted over a small peeling interface area. In short, the fabric layer 12 and film layer 24 can't stretch and peel in the reinforcement member 22 area.

Further, each reinforcement member 22 may be generally of an H-like shape, and the dressing 10 may include a recess 30 in the fabric layer edge 14 corresponding with each H-like shaped reinforcement member 22. Alternatively, the reinforcement member 22 may be one continuous member having a shape that corresponds with the shape and location of each recess 30. The shape of the reinforcement member(s) 22 is such that each reinforcement member spreads pulling/peeling forces exerted on the dressing assembly 10 during use so that these forces do not tear the dressing assembly 10 from a patient's skin. Each reinforcement member 22 may have an adhesive side 32 and an opposite non-adhesive side 34, the non-adhesive side 34 being adhered to the fabric layer adhesive side 16. Similar to the fabric layer, the adhesive on the reinforcement member adhesive side 32 may be any suitable medical grade adhesive.

At least one slit 36 may disposed in the fabric layer edge 14. In the embodiment shown in FIG. 1, the dressing 10 includes one medially disposed slit 36. The slit(s) 36 are useful to aide in securing the dressing 10 about the knuckles and fingers of a patient's hand. The slit(s) 36 allow the dressing 10 to be firmly secured around curved, irregular surfaces. Each slit 36 may be disposed along a length of the fabric layer edge 14 generally opposite the reinforcement member(s) 22. Each slit 36 may be secured by a temporary connector. Each temporary connector may be, for example, a very small piece of fabric material connected to the fabric layer 12 between each slit 36 and the fabric layer edge 14. Each temporary connector secures the fabric layer 12 about each slit 36 until a threshold force is applied to the temporary connector. When the temporary connector is broken, the slit 36 is opened. Each slit 36 may be a cut line or alternatively may be a perforated line. The slits 36 that are perforated lines are opened by tearing the perforations. In the embodiment shown in FIG. 1, the slit 36 is a cut line. A nurse can choose, or not, one or more slits to accommodate adherence to sometimes very complicated surface anatomy.

A plurality of recesses 38 may be located in the fabric layer edge 14. The recesses 38 may be disposed along a length of the fabric layer edge 14 generally opposite the reinforcement member(s) 22. In the embodiment shown in FIG. 1, the dressing 10 includes two recesses 38. The recesses 38, similar to the slits 36, aide in securing the dressing over curved surfaces such as the surfaces about a patient's knuckles and fingers. The recesses 38 may also be aligned with the slits 36 in order to cooperate with the slits in aiding to secure the dressing 10 around curved surfaces. Also, for certain uses of the dressing 10, one of the recesses 38 may be used as a receiver for a bend of medical tubing extending from a catheter disposed underneath the dressing. In particular, the embodiment shown in FIG. 1 is arranged for such a use. This embodiment of the dressing is intended for use with catheters connected to straight extension sets wherein the tubing must be bent approximately 180 degrees to route the tubing up an arm of a patient. For example, tubing connected to a straight extension set could exit from underneath the dressing 10 at the slit 36, turn in a 180 degree bend, and return to the underside of the dressing within the recess 38.

At least one perforation line 40 may extend inwardly from the fabric layer edge 14. Each perforation line 40 may be disposed along a length of the fabric layer edge 14 adjacent the reinforcement member(s) 22. The perforation lines 40 can be separated/torn prior to the dressing being secured to a patient's skin. The torn perforation lines 40 help to allow the dressing 10 to be secured to curved and/or uneven surfaces of a patient's body such as around the base of a patient's thumb and/or between a patient's thumb and index finger. A landmark notch 42 may be located along the fabric layer edge 14 contiguous with each of the perforation lines 40 for indicating the location of the perforation lines. This is important as the perforation lines 40 can be difficult to see and locate without careful inspection of the dressing 10. The landmark notches 42 may be, for example, V-shaped as shown in FIG. 1.

The dressing 10 may have a central axis 44 that spatially divides the dressing 10 into first and second portions 46, 48, the first and second portions being mirror images of each other. Since the first and second portions 46, 48 are mirror images, the dressing 10 may be easily used on either the right-hand side or left-hand side of a patient, or inboard or outboard on either the left or right hand. The dressing 10 may also have a generally rectangular or square shape and may be approximately 4 inches by 4 inches in size, yet variations in size and shape are within the scope of the invention.

The dressing 10 may also include a release liner 50 having a tackless side 52 contacting the adhesive side of the film layer 24 and/or fabric layer 12. The release liner 50 generally extends to the fabric layer edge 14. As shown in FIGS. 2 and 3, the release liner 50 may have a butterfly shape and may include a first piece 54 and a second piece 56. The first and second pieces 54, 56 may be folded such that each of the first and second pieces have a tab 58, 60 formed by the fold 62. One of the pieces 54, 56 can be released from the dressing 10 to expose the adhesive side of the film layer 24 and/or fabric layer 12 without tampering with the other piece. This is advantageous when applying the dressing 10 to a patient because it allows for half the dressing to be fixed to a patient's skin without the other half inadvertently and prematurely sticking to the patient's skin, a nurse's glove, or to the dressing itself. The tabs 58, 60 facilitate removal of each piece 54, 56 of the release liner 50 by providing a free extension of release liner material that may be easily grasped by a user.

Figure 4:
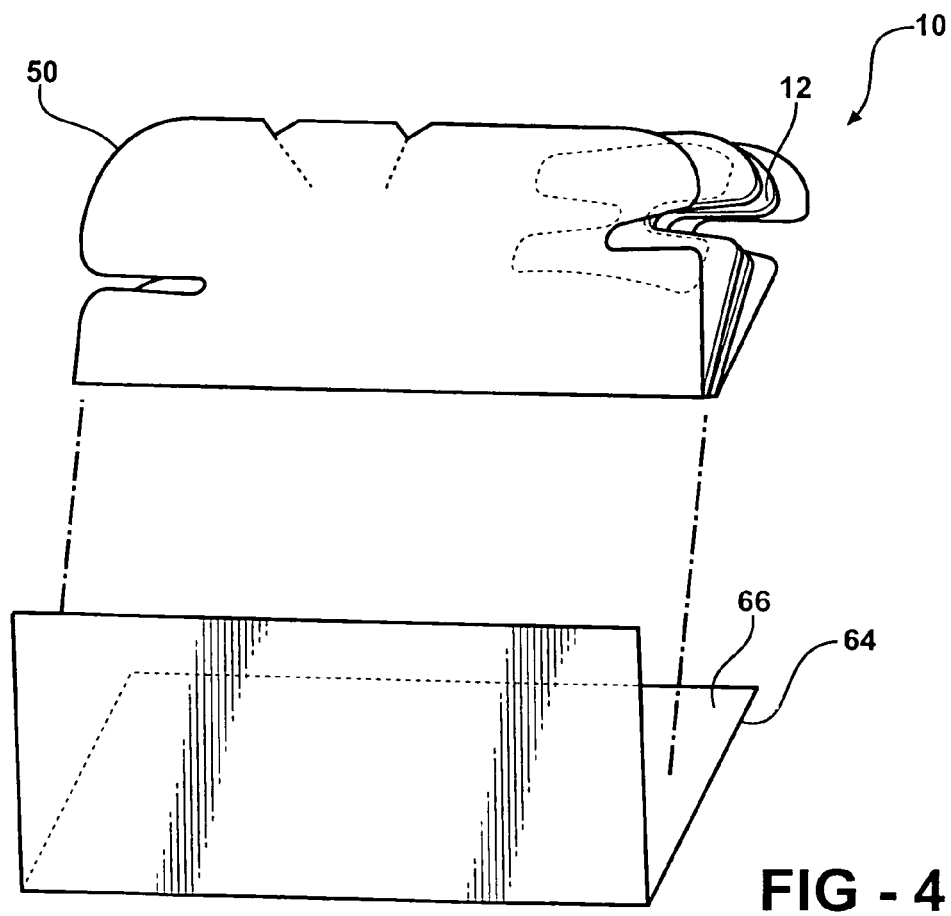
FIG. 4 is a perspective view of the PIV dressing assembly of FIG. 1 illustrating a wallet of the assembly.

As shown in FIG. 4, the dressing assembly 10 may further include a wallet 64, wherein the dressing is foldable and insertable in the wallet 64. To accommodate a dressing small size and thus a small IV start kit sterile package, the dressing 10 may be folded along the central axis 44 (as seen in FIG. 1) such that the fabric layer 12 is folded to the inside and the release liner 50 is on the outside. The wallet 64 may be a folded piece of release liner. The tackless side 66 of the release liner may be folded inward, and the folded dressing may then be inserted into the wallet 64 such that any exposed adhesive on the folded dressing contacts the tackless side 66 of the wallet 64. This prevents the dressing from becoming stuck and/or permanently attached to the wallet 64, or from touching anything else packed in an IV start kit.

Figure 5:
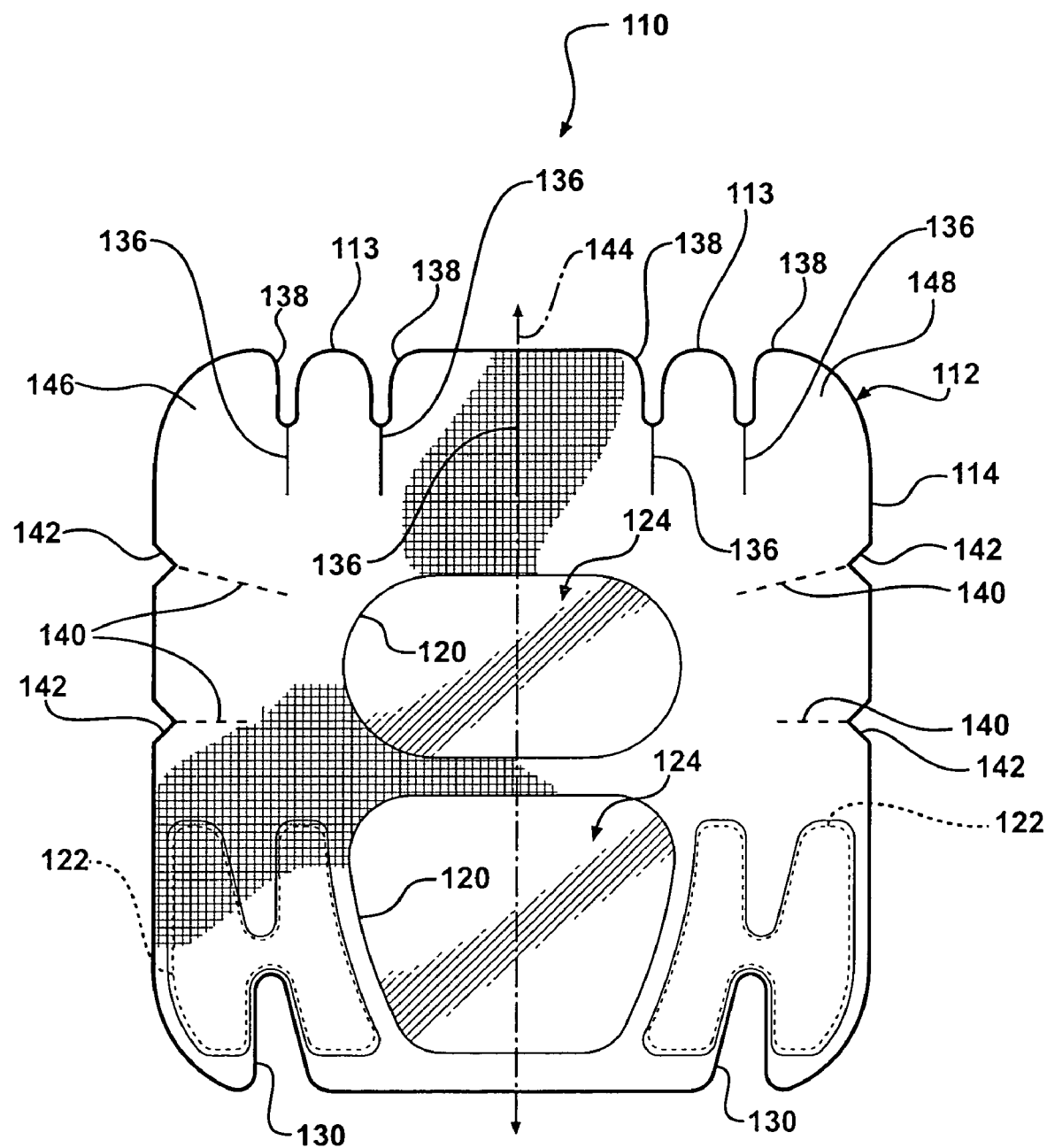
FIG. 5 is a plan view of an alternative embodiment of a PIV dressing assembly in accordance with the present invention.

Turning to FIG. 5, in a second embodiment of the present invention, the dressing 110 includes four recesses 138 in the fabric layer edge 114 disposed along a length of the fabric layer edge 114 generally opposite the reinforcement members 122. The dressing 110 also includes five slits 136 disposed in the fabric layer edge 114 along a length of the fabric layer edge 114 generally opposite the reinforcement members 122. One of the slits 136 is a medially disposed slit similar to the slit in the first embodiment that is disposed along the central axis 144. Each of the other four slits 136 is aligned with one of the recesses 138. The slits 136 may be cut lines or perforated lines, and may be secured by a temporary connector as described above. As in the first embodiment, the slits 136 and recesses 138 allow the dressing 110 to be firmly secured around curved, irregular surfaces such as fingers and knuckles.

A portion 113 of the fabric layer edge 114 may have a curved shape disposed along a length of the fabric layer edge opposite the reinforcement members 122. This further helps in fitting the dressing 110 about knuckles and fingers. The dressing 110 may otherwise include any combination of the other features described in the first embodiment 10. Similar features are similarly numbered (e.g. 20, 120). The embodiment shown in FIG. 5 is specifically arranged for use with catheters connected to angled connectors/extension sets wherein medical tubing connected to the extension set must only be bent approximately 90 degrees to route the tubing up an arm of a patient. In this arrangement, the tubing running from the catheter and connector remains underneath the dressing until it exits from underneath the dressing about the notch 130. Hence, the bend in the tubing is kept completely underneath the dressing 110, allowing a total closure and microbial barrier entirely 360 degrees around the insertion site, something rarely achieved with prior art dressings.

Figure 6:
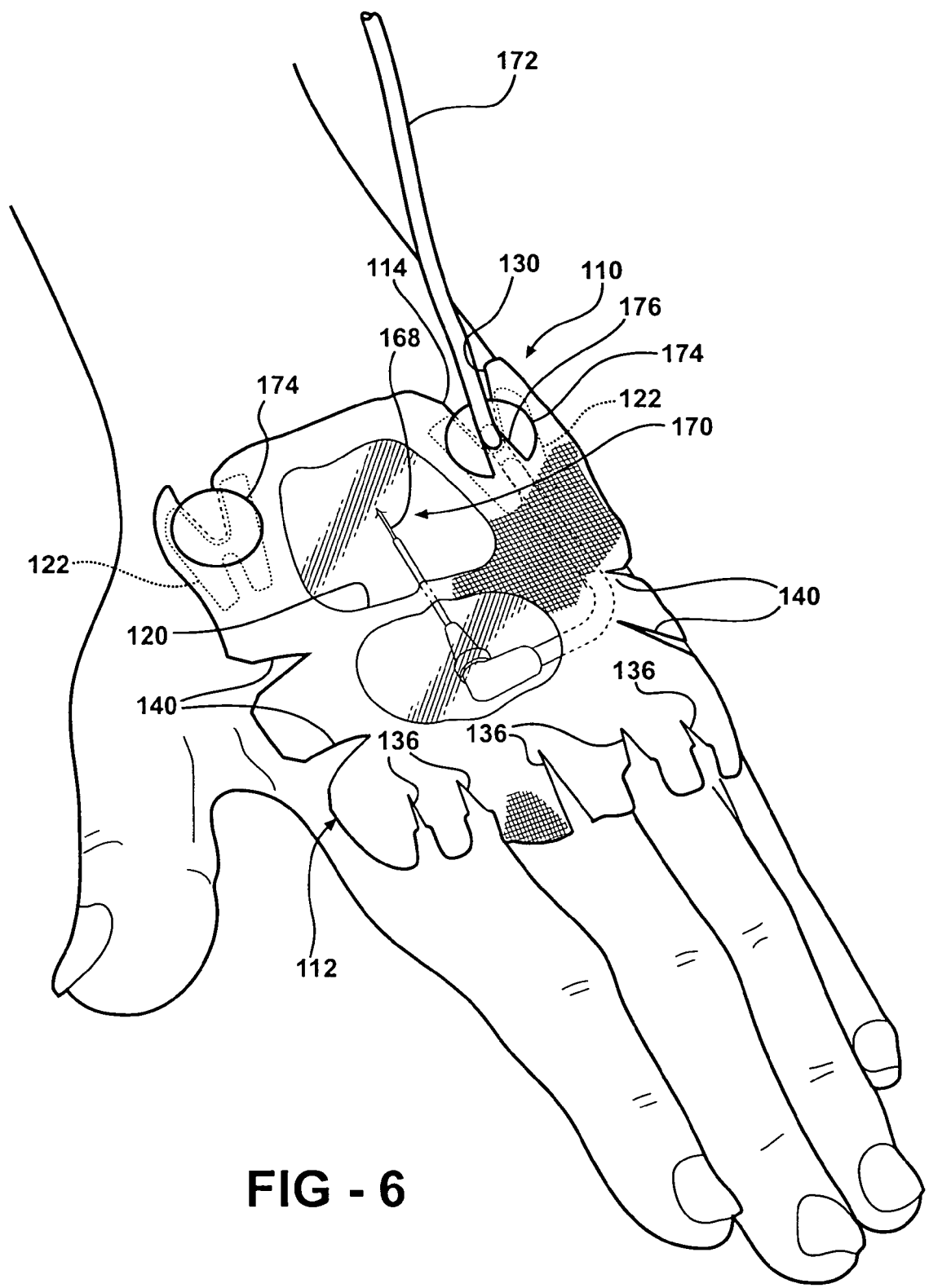
FIG. 6 is an environmental view of the PIV dressing assembly of FIG. 5 applied about a PIV catheter insertion site.

Turning now to FIGS. 5 and 6, the dressing assembly 110 may be used to protect a PIV catheter insertion site and to secure a catheter and associated tubing 360 degrees about the insertion site over significant radial distances up to two inches in any direction from the insertion point. The use of the present invention will first be described with reference to the second embodiment 110, in which the dressing 110 is used to protect and secure a catheter connected to medical tubing by an angled connector. First, a catheter 168 is inserted into a PIV insertion site 170 of a patient. Then, medical tubing 172, which in this case is connected to a connector/extension set such as an angled connector, is connected to the catheter 168. Once the catheter 168 and tubing 172 are in place, one piece of the release liner may be removed from the dressing assembly 110 to expose the adhesive side of the fabric layer 112 and/or the film layer 124. Prior to removal of the piece of release liner (or less preferably, after the removal of the piece of release liner), some or all of the temporary connectors and/or perforated lines may be broken/separated to open the slits 136 along the edge 114 of the dressing assembly 110. Similarly, the dressing assembly 110 may be torn along one or more of the perforation lines 140 so that the dressing may be easily placed around curved, irregular contours of a patient's body such as around a patient's hand, fingers, and knuckles. The exposed half of the dressing assembly 110 may then be placed on a patient's skin such that one of the openings 120 is centered over the catheter insertion site 170.

After the first half of the dressing assembly 110 is secured to the patient's skin, the other piece of release liner may be removed to expose the adhesive side of the dressing. Then, the newly exposed piece of the dressing 110 may be secured to the patient's skin. During securement of the dressing assembly 110, care must be given to positioning the tubing 172 so that the tubing exits from underneath the dressing assembly 110 within one of the recesses 130 corresponding in location to one of the reinforcement members 122. This insures that the tubing 172 is properly secured so that pulling forces on the tubing are much less likely to unpeel the dressing 110 from the patient's skin.

The dressing assembly 110 may also include at least one closure member 174. Each closure member 174 has an adhesive side and an opposite non-adhesive side. Each closure member 174 is disposable on the fabric layer 112 about the fabric layer edge 114 at a location corresponding with a reinforcement member 122 and recess 130. One closure member 174 may include a recess 176, and each closure member 174 may have a generally circular shape. The closure member(s) 174 may be made of a foam padding or similar. In the embodiment shown in FIG. 6, the dressing assembly 110 includes two closure members 174. The closure member 174 having the recess 176 is disposable about the tubing 172 where the tubing exits from underneath the dressing 110. The other closure member 174 may be placed over the recess 130 in the dressing corresponding with the other reinforcement member 122 to close over the recess 130. When adhered to the dressing, the closure members 174 may also be used as a surface to write pertinent information such as the starting date and time of application of the dressing. Only the easily rippable foam closure 174 completely surrounds the tubing 172 facilitating easy removal of the dressing 110 from the tubing 172. This is in contrast to the difficulty of removing prior art taping wrapped 360 degrees around catheter hubs and tubings.

Figure 7:
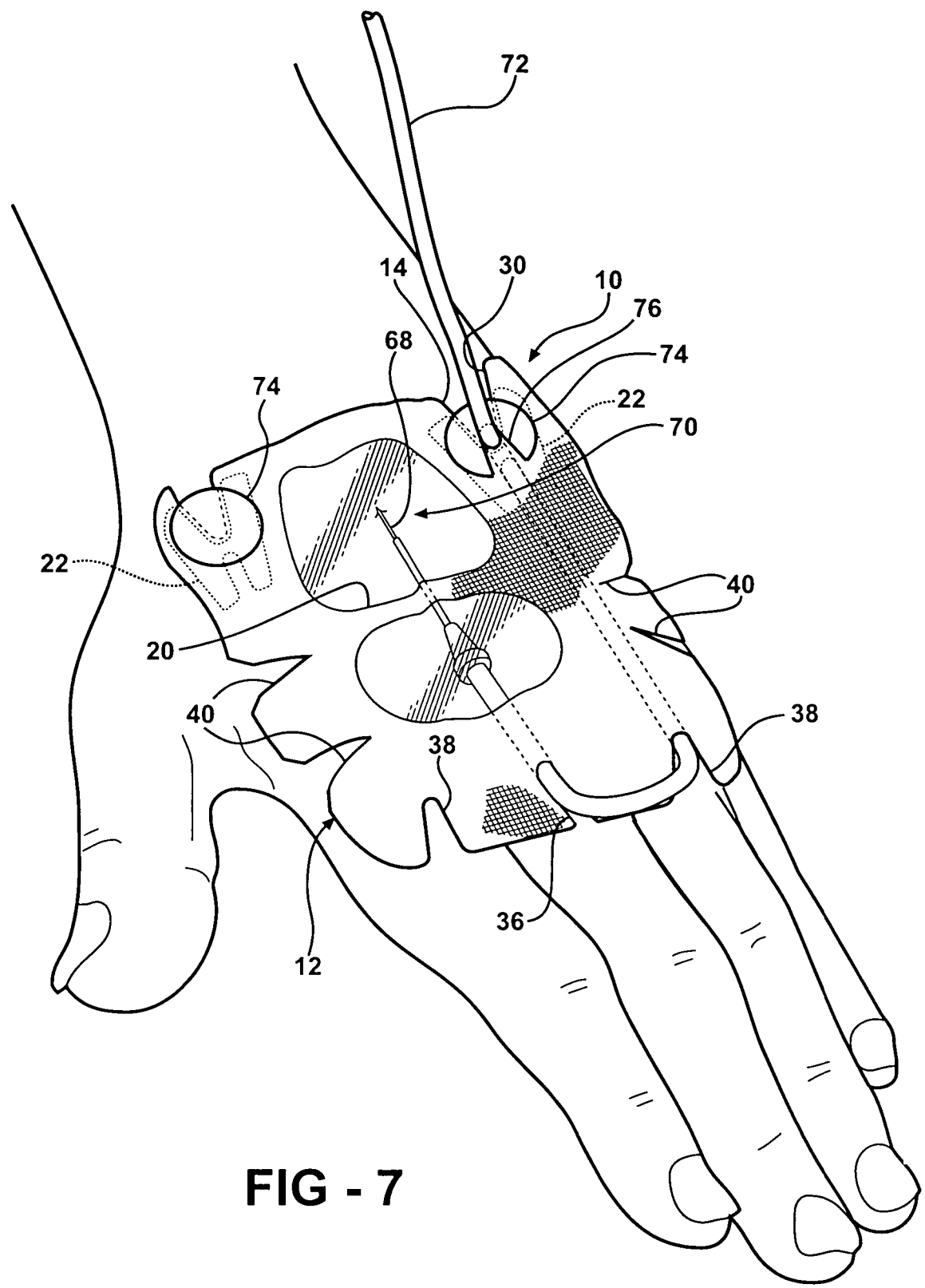
FIG. 7 is an environmental view of the PIV dressing assembly of FIG. 1 applied about a PIV catheter insertion site.

Turning now to FIGS. 1 and 7, the use of the present invention is illustrated with respect to the first embodiment 10, in which the dressing 10 is used to protect and secure a catheter 68 connected to medical tubing 72 by a straight extension set. In this case, after insertion of the catheter 68 at the insertion site 70, one piece of the release liner 50 may be removed from the dressing assembly 10 to expose the adhesive side of the fabric layer 12 and/or the film layer 24. As with the second embodiment 110, one or more of the perforation lines 40 may be torn prior to removal of the piece of release liner 50. The exposed half of the dressing assembly 10 may be placed on a patient's skin such that one of the openings 20 is centered over the catheter insertion site 70. Further, the dressing should be positioned such that the central axis 44 generally runs along the catheter 68 and tubing 72.

After the first half of the dressing assembly 10 is secured to the patient's skin, the other piece of release liner 50 may be removed to expose the remainder of the adhesive side of the dressing. Before securing the remainder of the dressing 10 to the patient's skin, the tubing 72 is positioned within the slit 36 and then bent so that it makes an approximately 180 degree turn. As the free portion of the dressing 10 is brought towards the patient's skin, the tubing 72 is positioned such that the tubing is disposed between the recess 38 at the 180 degree bend. Also, further up the length of tubing 72, the tubing is positioned between the reinforcement member 22 and the recess 30. When the dressing 10 is then adhered to the patient's skin, the tubing 72 runs underneath the dressing generally between the catheter 68 and the slit 36 as well as between the recess 38 and the recess 30.

The dressing assembly 10 may also include at least one closure member 74. In FIG. 7, the dressing assembly 10 is shown with two closure members 74. The closure members 74 have similar features and uses as the closure members 174 described in reference to the second embodiment 110.

Although the invention has been described by reference to specific embodiments, it should be understood that numerous changes may be made within the spirit and scope of the inventive concepts described. Accordingly, it is intended that the invention not be limited to the described embodiments, but that it have the full scope defined by the language of the following claims.

What is claimed is:

1. A PIV window dressing assembly for the protection of a PIV catheter insertion site that is interchangeably usable on both a right or left-hand side insertion site and that resists detachment from a patient's skin during use, the dressing assembly comprising:
    a fabric layer that is bounded by an edge, said fabric layer having an adhesive side, an opposite non-adhesive side, and at least one opening therein to allow for viewing therethrough;
    at least one-reinforcement member disposed between the fabric layer edge and said opening, said reinforcement member being adhered to the fabric layer adhesive side and being generally of an H-like shape, and said reinforcement member distributing pull forces exerted on said dressing assembly over a larger surface area and resisting peeling of said dressing assembly from a patient's skin;
    a recess in the fabric layer edge corresponding with the location of each H-like shaped reinforcement member; and
    a transparent film layer having an adhesive skin adhering side and an opposite non-adhesive side, said film layer closing each of said at least one opening in said fabric layer, said film layer non-adhesive side being adhered to the fabric layer adhesive side.

2. The PIV dressing assembly of claim 1, wherein each of said at least one reinforcement member has an adhesive side and an opposite non-adhesive side, the reinforcement member non-adhesive side being adhered to the fabric layer adhesive side.

3. The PIV dressing assembly of claim 1, including at least one slit in the fabric layer edge.

4. The PIV dressing assembly of claim 3, wherein each said at least one slit is disposed along a length of the fabric layer edge generally opposite said reinforcement member.

5. The PIV dressing assembly of claim 3, wherein each said at least one slit is one of a cut line and a perforated line.

6. The PIV dressing assembly of claim 1, including a plurality of recesses disposed along a length of the fabric layer edge.

7. The PIV dressing assembly of claim 6, wherein said recesses are disposed along a length of the fabric layer edge generally opposite said reinforcement member.

8. The PIV dressing assembly of claim 1, wherein a portion of the fabric layer edge has a curved shape disposed along a length of fabric layer edge opposite said reinforcement member.

9. The PIV dressing assembly of claim 1 including at least one perforation line extending inwardly from the fabric layer edge, said at least one perforation line being disposed along a length of the fabric layer edge adjacent said reinforcement member.

10. The PIV dressing assembly of claim 9 including a landmark notch along the fabric layer edge contiguous with each of said at least one perforation line for indicating the location of said at least one perforation line.

11. The PIV dressing assembly of claim 1, wherein said dressing assembly has a central axis that spatially divides said dressing assembly into first and second portions, said first and second portions being mirror images of each other.

12. The PIV dressing assembly of claim 1, wherein said dressing assembly is generally one of a rectangular and square shape.

13. The PIV dressing assembly of claim 1, including a release liner having a tackless side contacting said adhesive side of said film layer, said release liner generally extending to said edge of said fabric layer.

14. The PIV dressing assembly of claim 13, wherein said release liner includes a first piece and a second piece, said first and second pieces being folded such that each of said first and second pieces have a tab formed by the fold; whereby one of said pieces can be released from said dressing assembly without tampering with the other of said pieces.

15. The PIV dressing assembly of claim 1, including a wallet, wherein said dressing assembly is folded and inserted into said wallet.

16. The PIV dressing assembly of claim 15, wherein said wallet includes a folded release liner.

17. A PIV window dressing assembly for the protection of a Ply catheter insertion site that is interchangeably usable on both a right or left-hand side insertion site and that resists detachment from a patient's skin during use, the dressing assembly comprising:

a fabric layer that is bounded by an edge, said fabric layer having an adhesive side, an opposite non-adhesive side, and at least one opening therein to allow for viewing therethrough;

at least one reinforcement member disposed between the fabric layer edge and said opening, said at least one reinforcement member being adhered to the fabric layer adhesive side, said at least one reinforcement member; and distributing pull forces exerted on said dressing assembly over a larger surface area and resisting peeling of said dressing assembly from a patient's skin;

a recess in the fabric layer edge corresponding with the location of each said at least one reinforcement member;

a transparent film layer having an adhesive skin adhering side and an opposite non- adhesive side, said film layer closing each of said at least one opening in said fabric layer, said film layer non-adhesive side being adhered to the fabric layer adhesive side; and at least one closure member, each said at least one closure member having an adhesive side and an opposite non-adhesive side, wherein each said at least one closure member is disposable on said fabric layer about the fabric layer edge at a location corresponding with said at least one reinforcement member.

18. The PIV dressing assembly of claim 17, wherein one of said at least one closure member includes a recess.

19. The PIV dressing assembly of claim 17, wherein each closure member generally has a circular shape.

* * * * *